(12) United States Patent
Ardelean et al.

(10) Patent No.: US 8,544,340 B1
(45) Date of Patent: Oct. 1, 2013

(54) DEVICE FOR TESTING THIN SPECIMENS IN PURE BENDING

(75) Inventors: Emil V. Ardelean, Albuquerque, NM (US); Thomas W. Murphey, Albuquerque, NM (US); Gregory E. Sanford, Albuquerque, NM (US)

(73) Assignee: The United States of America as Represented by the Secretary of the Air Force, Washington, DC (US)

( * ) Notice: Subject to any disclaimer, the term of this patent is extended or adjusted under 35 U.S.C. 154(b) by 263 days.

(21) Appl. No.: 13/245,207

(22) Filed: Sep. 26, 2011

(51) Int. Cl.
*G01N 3/20* (2006.01)
(52) U.S. Cl.
USPC .............................................. 73/849; 73/860
(58) Field of Classification Search
USPC .......................................... 73/849, 856–860
See application file for complete search history.

(56) References Cited

U.S. PATENT DOCUMENTS

| | | | | |
|---|---|---|---|---|
| 5,305,634 | A * | 4/1994 | Suga et al. | 73/86 |
| 5,437,192 | A * | 8/1995 | Kawamoto et al. | 73/826 |
| 7,214,200 | B2 * | 5/2007 | Raney et al. | 600/584 |
| 7,708,703 | B2 * | 5/2010 | Raney et al. | 600/583 |

OTHER PUBLICATIONS

Sanford, et al "High Strain Test Method for Thin Composite Laminates" 16th Intl Conf Composite Structures, 2011.

* cited by examiner

*Primary Examiner* — Max Noori
(74) *Attorney, Agent, or Firm* — James M. Skorich; Kenneth E. Callahan

(57) ABSTRACT

An improved test fixture to evaluate thin composite laminates commonly used in deployable space structures. The fixture is designed to impart a pure moment into the coupon, a necessary improvement to prior test methods where results are obtained by fitting material properties in a nonlinear structural analysis of the test. Fixture mechanics allow for direct calculation of the coupon flexural modulus and allowable flexural strain based on two key measurements, fixture displacement and applied load.

2 Claims, 7 Drawing Sheets

DEVICE FOR TESTING THIN SPECIMENS IN PURE BENDING

STATEMENT OF GOVERNMENT INTEREST

The conditions under which this invention was made are such as to entitle the Government of the United States under paragraph 1(a) of Executive Order 10096, as represented by the Secretary of the Air Force, to the entire right, title and interest therein, including foreign rights.

BACKGROUND OF THE INVENTION

The invention relates generally to testing of flexure specimens to determine strain and elastic modulus, and in particular to a device designed to allow testing under pure bending conditions of thin composite laminates used as flexural elements.

Thin composite laminates are commonly used in deployable space structures. In application, the laminates are elastically folded to allow a structure to be compactly stowed during launch and subsequently deployed to an operational state once in orbit. This basic technology enables operational systems containing structures such as solar arrays, reflectors, antennas, and booms to be efficiently packaged and launched within the payload envelope of conventional launch vehicle fairings or within tightly allocated volume constraints common to compartmentalized payloads such as CubeSats.

While the use of composite laminates in deployable structures is widely acceptable, in operation they are subjected to strain levels and deformations outside of traditional composite structural applications. As such, their behavior is poorly understood, making deployable structure design and analysis extremely difficult. Currently, standardized ASTM test methods are used to determine composite material strengths and linear-elastic stiffnesses under traditional loading applications such as axial and transverse tension, compression, and shear. Data from these tests yield accurate, basic properties that are useful for laminate design, but they fail to characterize the nonlinear constitutive behavior over the full strain range common to deployable structures.

Studies have shown that flexural loading will result in higher compressive and tensile strengths than are determined from traditional tensile and compressive coupon tests. Single fiber tests further support this behavior, showing significantly higher flexural strengths as compared to tensile strength data. Attempts at analytically quantifying these increased strengths have largely been ineffective or are not applicable to the thin laminates used in deployable structures. For example, the commonly used Weibull statistical model under predicts flexural strength, while single fiber data does not consider structural stabilization or the role of the laminate matrix. Furthermore, the extrapolation of classical bending theory, which assumes linear-elastic behavior, is of little value due to nonlinear composite stiffening and softening with increasing and decreasing strains respectively. Finally, the matter is further complicated by laminate thickness concerns for composites in bending. Thinner specimens have been found to have higher compressive strengths due to the steep stress gradient through the specimen thickness because of the close proximity of fibers under tension and compression.

The current method for such testing is demonstrated in FIG. 1 in which two parallel platens 2, 3 are pressed together with the specimen 1 between them. The applied force F measured by the load cell 4 and the platen separation data d are used to calculate the applied moment and specimen curvature by using the rather complex Euler elastic analytical model. This test method does not generate a pure stress state in the specimen and does not allow a direct measurement of curvature, bending moment, or strain.

SUMMARY

The device is designed for testing under pure bending conditions thin composite laminate specimens used as flexural elements in deployable structures used in space applications. While the use of composite laminates in deployable structures has become widely acceptable, they are subjected to large deformations with strain levels well beyond what classical theories predict. This test device was designed to be used in an ordinary test frame. The test specimen is clamped between two carts with rotating bearings located on two parallel tracks allowing horizontal movement. Each cart has a near vertical arm with a third rotating bearing at the upper end. Cross members apply force to the vertical arms causing the carts to move and stressing the specimen into an arc of up to 180 degrees.

The relationship between bending moment and specimen curvature allows calculation of strain and elastic modulus. The moment and curvature in the specimen can be calculated from the fixture geometry of the device and two direct measurements: applied axial load and cross member displacement.

DESCRIPTION OF THE PREFERRED EMBODIMENT

Figure 1:
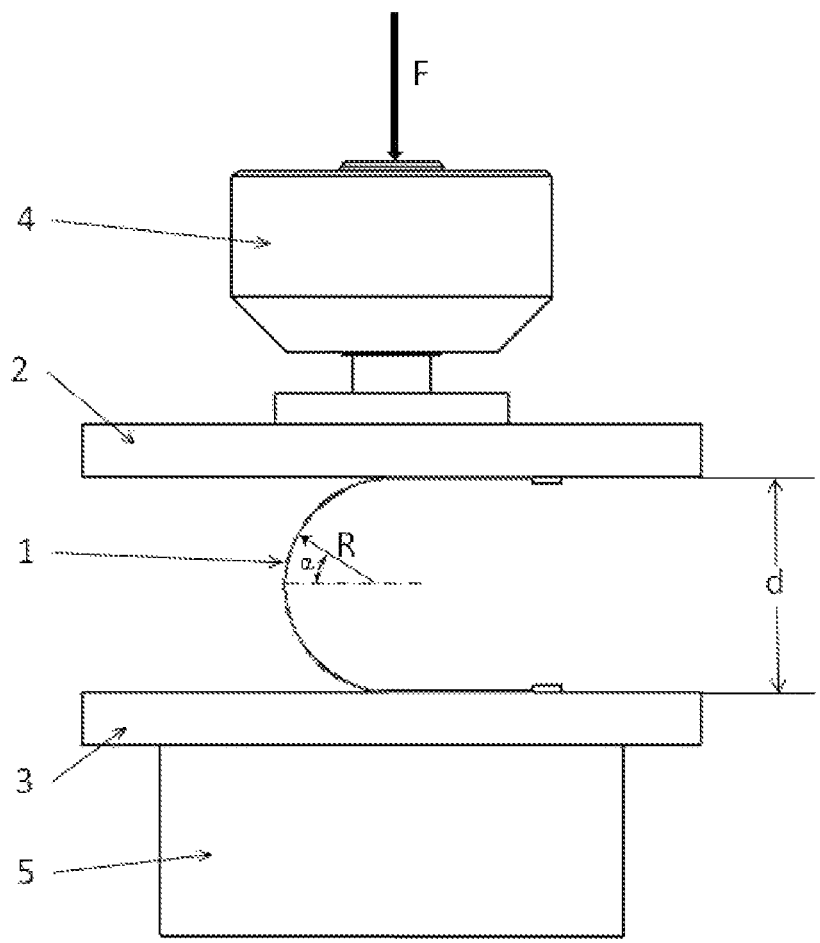
FIG. 1 is a schematic demonstrating the current method of testing flexure specimens.
Figure 2:
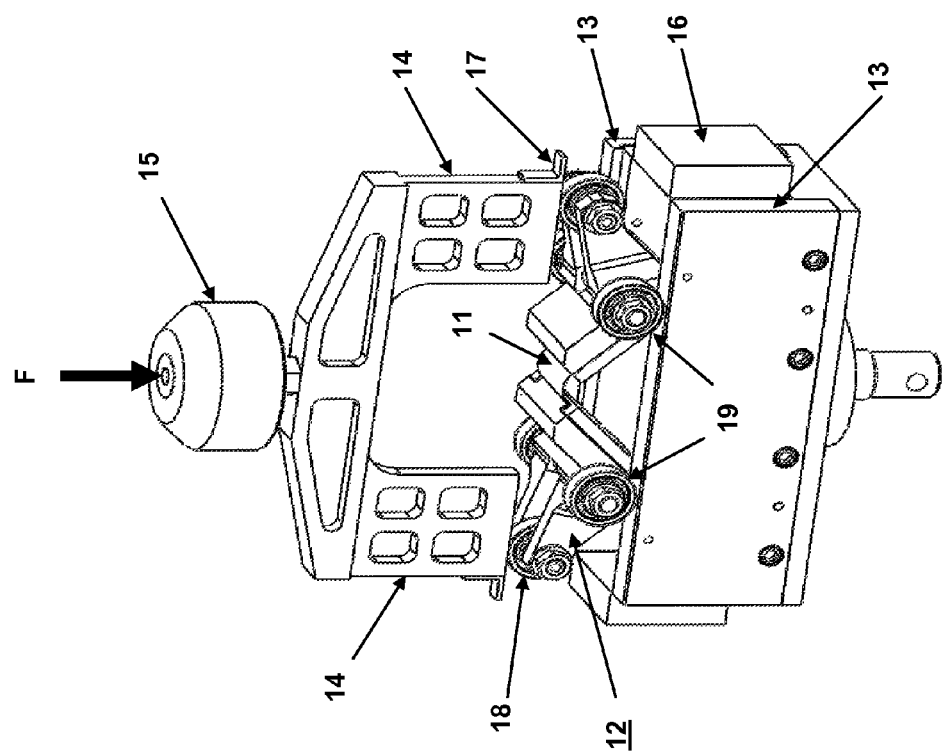
FIG. 2 is a 3-D schematic of the pure moment test device during a test.
Figure 3:
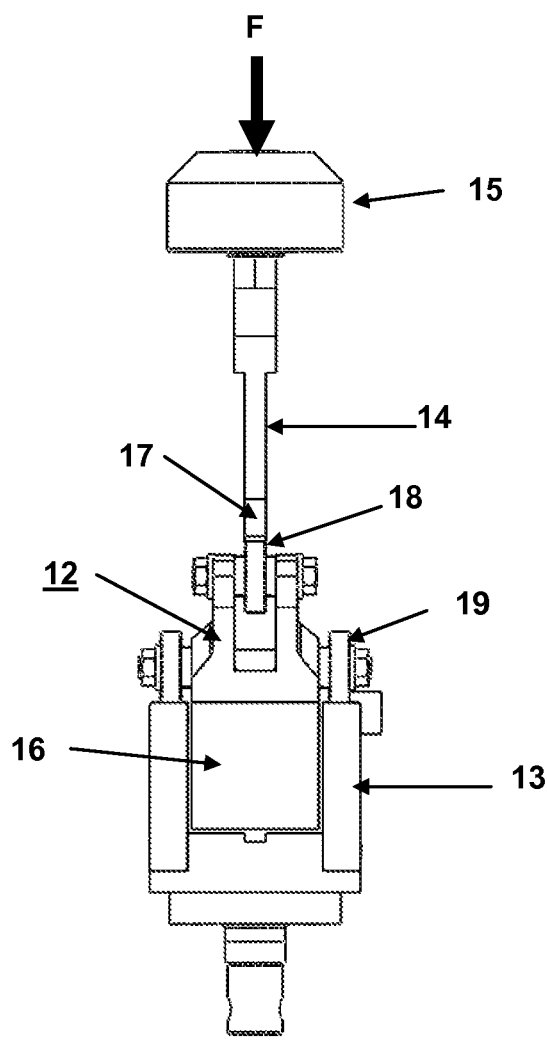
FIG. 3 is a side-view diagram of the test device.
Figure 4C:
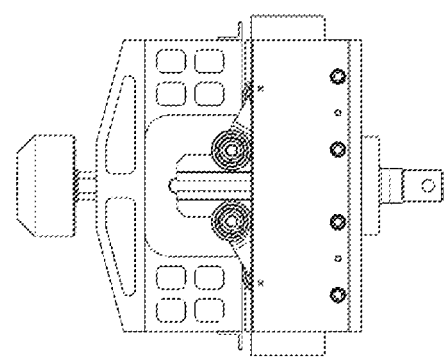
FIG. 4c is a front-view diagram of the device during a test showing the maximum cart displacement in which the coupon is bent through a 180 degree arc.
Figure 4B:
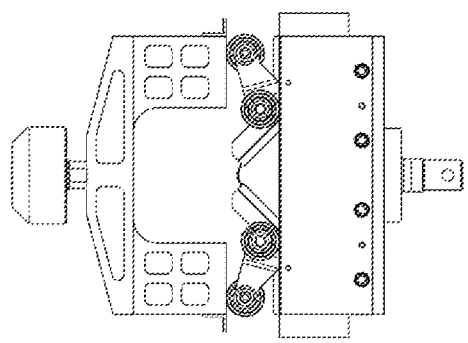
FIG. 4b is a front-view diagram of the device at an intermediate stage of a test sequence.
Figure 4A:
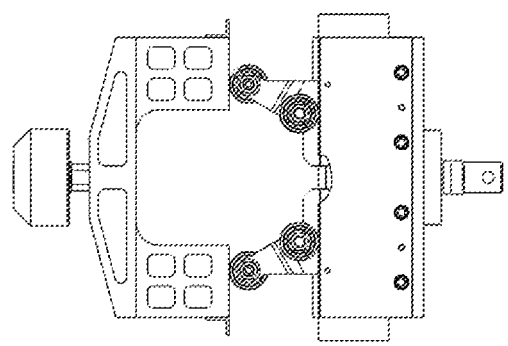
FIG. 4a is a front-view diagram of the device at the initial test setup configuration.

An improved test fixture has been designed that allows pure moment to be imparted into the composite test coupon (thin composite laminate specimen). As shown in FIG. 2, the test fixture is used to clamp a coupon 11 between two rotating carts 12 that are driven downward by the cross members 14 pushing downward upon the bearings 18 at the end of the near vertical arms of the carts. As the cross members 14 move downward, the carts rotate about the axes of the lower bearings 19, thus apply the bending moment on the coupon 11. The carts are very stiff compared with the coupon and are considered perfectly rigid. As the coupon deforms, the carts translate along tracks 13 until they reach the extreme position that corresponds to a coupon arc angle of 180° or until the coupon fails. Load (F) and cross member displacement are measured to calculate the applied moment and curvature. The load cell 15 placed between the cross member and the test frame is used to measure the applied load F. Laser displacement sensors 16, placed at each end of the tracks, are used to measure cross member displacement by reflecting off the targets 17 attached to the cross members. In addition to moment and curvature calculation, data from the two sensors can be used to verify the two carts are rotating in concert, which indicates the load is applied uniformly between the carts. FIG. 3 is a side view of the test fixture. Three stages of a test sequence is shown in FIG. 4. Initially (4a) the cross members are just in contact with the upper bearings of the two carts and there is no stress on the coupon. FIG. 4b shows an intermediate step in the test sequence in which the upper bearings are pressed downward by the cross members and the coupon is bent in an arc. FIG. 4c shows the maximum downward displacement of the cross members causing a 180 degree arc in the coupon, assuming it had not earlier broken.

Non-contact displacement sensors were chosen to avoid additional contribution (pollution) to the force registered by the load cell. Micro-Epsilon laser displacement sensors, with a measurement range of 100 mm, were selected for this application. Although not as precise, the test frame crosshead displacement data can be used to verify the data from the laser position sensors.

Three ball bearings 18, 19 provide low-friction rotation and minimal cart-to-track contact for each of the two carts. Standard electric motor type bearings with C-3 radial clearance were found to have sufficiently low breaking and rotational friction. The bearings are double shielded to prevent composite debris and other contaminates from stalling the bearing mechanism. To prevent degradation of the fixture corrosion, all parts, including the ball bearings, are made out of 17-4PH stainless steel. Those skilled in the art will appreciate that careful fixture alignment of carts, coupon, and cross members is required for successful test results.

Figure 5:
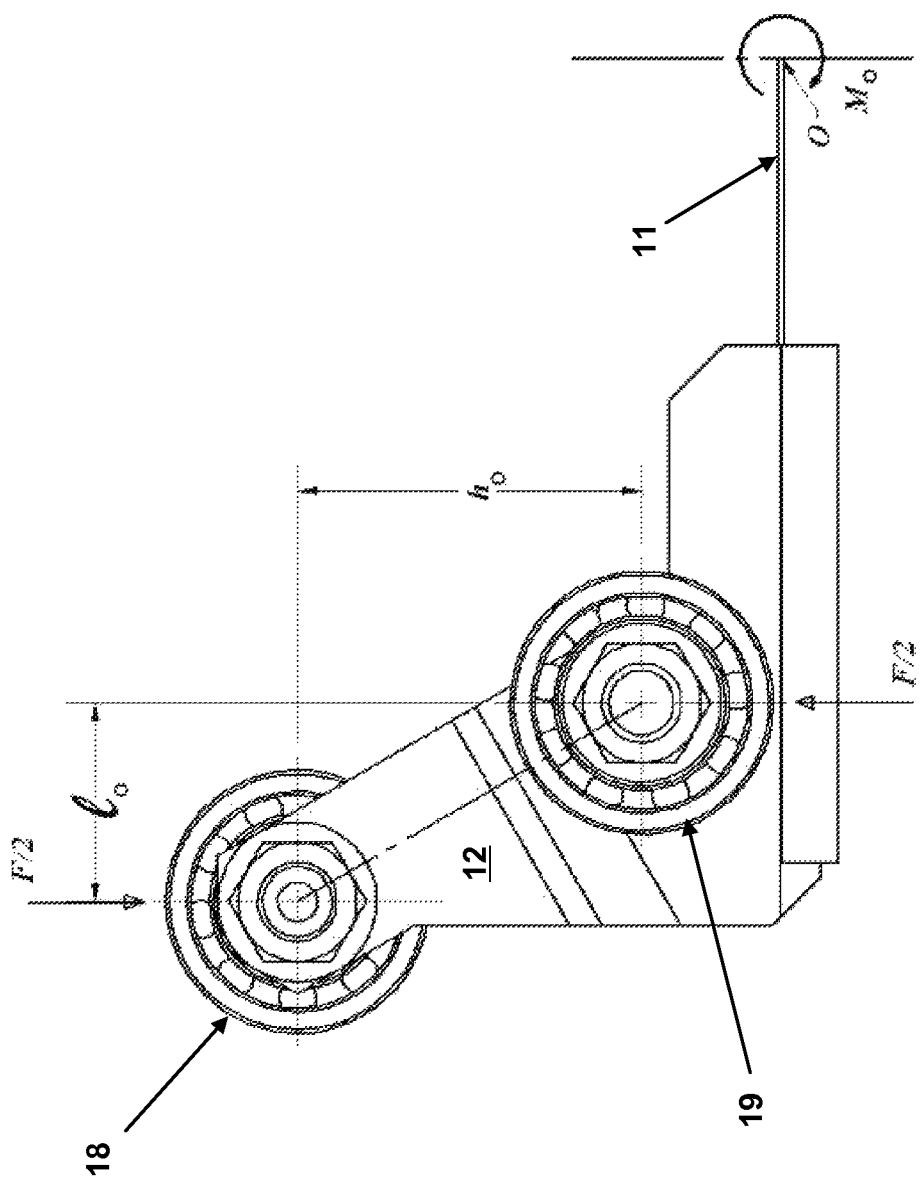
FIG. 5 is a detailed diagram of a cart in the initial test setup position.

The moment and curvature in the coupon are calculated from the fixture geometry and the two direct measurements: applied axial load and cross member displacement. Based on the test setup and the cart's free body diagram, shown in FIG. 5 and FIG. 6, the moment in the coupon, $M_o$, can be found from the applied load, F. As the cross members translate downward and apply load, the carts will begin to rotate, creating the pure moment found in Eq. (1).

$$M_o = \frac{F}{2} l \quad (1)$$

Figure 6:
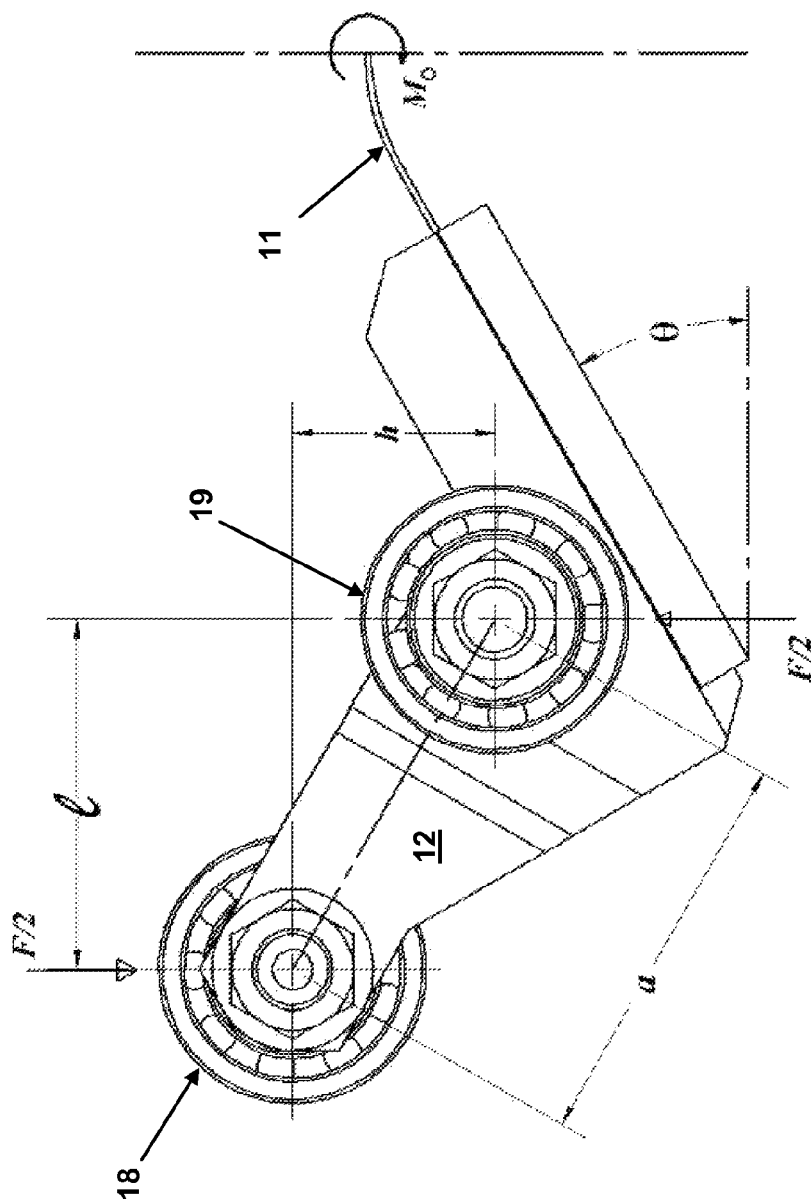
FIG. 6 is a detailed diagram of a cart shown in a rotated position during an intermediate stage of a test sequence.

The kinematic variables and constants of motion during testing are shown in FIG. 6. The initial horizontal and vertical distances between the two bearings, $l_o$ and $h_o$ from FIG. 5, and the constant distance between the bearings, a, are known from the cart geometry. As the cross member pushes on the upper bearings, the carts rotate about the lower bearing axis, and $\theta$ increases. The cross member location is measured directly with laser displacement sensors, allowing for the simple calculation of l shown in Eq. (2).

$$l = \sqrt{a^2 - h^2} \quad (2)$$

Finally, by combining equations (1) and (2), a relationship for the applied pure moment as a function of the measured and constant testing parameters is:

$$M_o = \frac{F}{2} \sqrt{a^2 - h^2} \quad (3)$$

Figure 7:
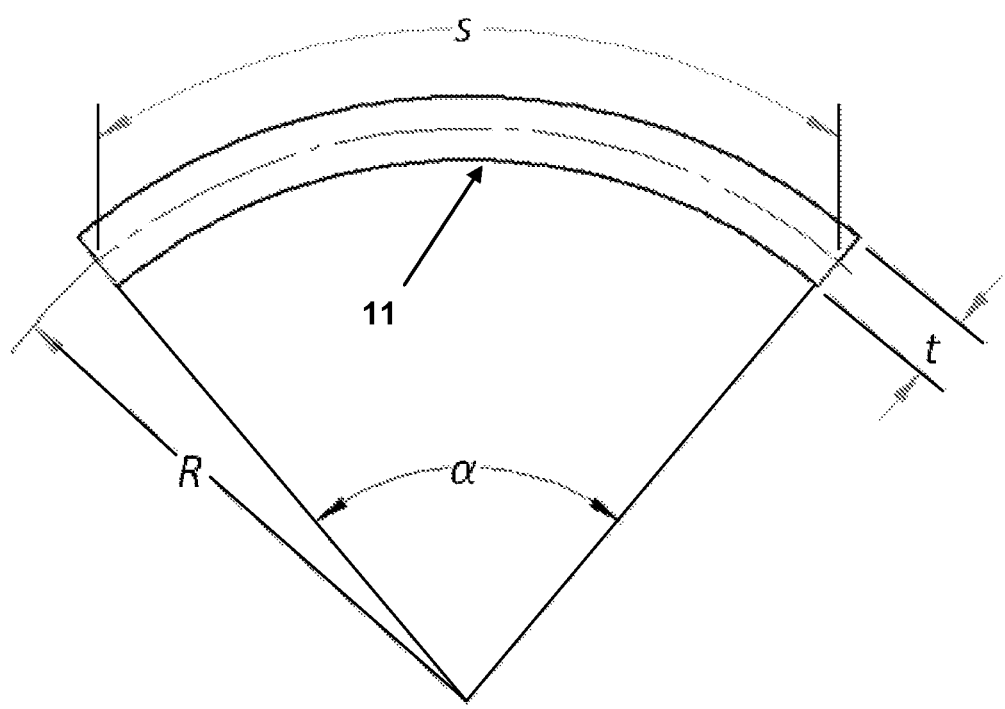
FIG. 7 shows the coupon geometry during a test.

The strain, $\epsilon$, of a deformed element can be represented in terms of the distance from the neutral axis and the element's radius of curvature. Both carts are under equal load, bending the coupon as shown in FIG. 7. The angle for the arc is twice the angle through which each cart rotates, or $\alpha = 2\theta$. The deformed segment has a radius of curvature, R, as shown.

From the equations derived above, the moment vs. curvature relationship can be calculated. By fitting the data linearly and dividing the slope of the linear fit line by moment of inertia we find the flexural modulus of elasticity for the specific material in question. Curvature, k, is known to be:

$$k = \frac{M}{EI}, \text{ or, } k = \frac{2\theta}{s} = \frac{\alpha}{s}.$$

From the mechanics of a simple beam in bending, the coupon strain can be expressed as shown in Eq. (4), where y is the distance from the coupon's neutral axis.

$$\varepsilon = \frac{y}{R} \quad (4)$$

The maximum (tensile) and minimum (compressive) strains will occur at the coupon surfaces, where $$y = \pm \frac{t}{2}.$$

These strains are:

$$\varepsilon_{max} = \frac{\frac{t}{2}}{R} = \frac{t}{2R} \quad (5)$$

and, $$\varepsilon_{min} = \frac{\frac{-t}{2}}{R} = \frac{-t}{2R} \quad (6)$$

From previous experiments, or from baseline testing of new materials, a good understanding of the thin composite failure strains can be generated. With that information and the equations above, the unstrained coupon length, s, can be pre-set to ensure coupon failure occurs prior to reaching the mechanical testing limit where $\alpha = 180°$. The expression for the unstrained coupon length as a function of $\alpha$ is shown in Eq. (7), and the expression evaluated at $\alpha = 180° = \pi$ is shown in Eq. (8).

$$s = R \cdot \alpha \quad (7)$$

$$s = R \cdot \pi \quad (8)$$

Substituting the solution of $$R = \frac{s}{\pi}$$

from Eq. (8) into Eq. (5), the unstrained coupon length, also the initial cart spacing, can be found for a maximum, predetermined strain value:

$$s = \frac{\pi t}{2\varepsilon_{max}} \quad (9)$$

It should be noted that the above coupon length calculation is based on a linear material assumption, something that is not the case for composite materials. In this application, however, the linear approximation is sufficient to estimate the appropriate coupon length.

An important advantage of this test fixture is that a wide range of coupon sizes can be tested without any fixture changes. In addition, the fixture can be easily scaled for larger or smaller samples, or of different aspect ratio. The force required to produce the bending moment, however, can vary significantly as a function of the specimen thickness and its elastic modulus. Therefore, the correct load cell capacity must be selected to cover the test coupon matrix.

The invention claimed is:

1. A test fixture used to determine bending properties of thin material specimens, said test fixture comprised of:
   a. two rotating carts, each cart comprised of a horizontal arm rigidly connected to a near vertical arm making an angle of approximately 120 degrees at the connection point, both arms being approximately the same length and thickness, a rotating bearing attached to each side of said cart near said connection point and a rotating bearing mounted at the end of said near vertical arm opposite said connection point;
   b. a specimen to be tested clamped at one end to the end of the horizontal arm opposite to said connection point of a first cart and the opposite end of said specimen clamped to the end of the horizontal arm opposite to said connection point of a second cart;
   c. two parallel tracks upon which said rotating bearings located at said connection point of said carts can rotate to move said carts horizontally;
   d. a cross member positioned vertically over the rotating bearing at the upper end of the near vertical arm of each cart and capable of being moved up or down vertically in response to an applied force and each cross member having a laser displacement sensor target attached;
   e. a force sensor to measure said applied force;
   f. a base upon which said tracks are rigidly attached;
   g. laser displacement sensors for measuring the displacement between said cross members and said base in conjunction with said sensor targets, whereby properties of said specimen may be calculated from the direct measurement of the applied force and the cross member displacement.

2. The test fixture of claim 1, wherein the test specimens are thin composite laminate materials.

* * * * *